US012285522B2

(12) United States Patent
McConville

(10) Patent No.: US 12,285,522 B2
(45) Date of Patent: *Apr. 29, 2025

(54) THERMALLY GELLING DRUG FORMULATIONS

(71) Applicant: UNM RAINFOREST INNOVATIONS, Albuquerque, NM (US)

(72) Inventor: Jason Thomas McConville, Albuquerque, NM (US)

(73) Assignee: UNM RAINFOREST INNOVATIONS, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/962,748

(22) Filed: Oct. 10, 2022

(65) Prior Publication Data

US 2023/0052945 A1 Feb. 16, 2023

Related U.S. Application Data

(63) Continuation of application No. 16/947,224, filed on Jul. 23, 2020, now Pat. No. 11,464,736.

(60) Provisional application No. 62/877,640, filed on Jul. 23, 2019.

(51) Int. Cl.
*A61K 9/00* (2006.01)
*A61K 31/192* (2006.01)
*A61K 31/4748* (2006.01)
*A61K 31/496* (2006.01)
*A61K 47/38* (2006.01)

(52) U.S. Cl.
CPC ............ *A61K 9/006* (2013.01); *A61K 31/192* (2013.01); *A61K 31/4748* (2013.01); *A61K 31/496* (2013.01); *A61K 47/38* (2013.01)

(58) Field of Classification Search
CPC . A61K 9/70; A61K 9/00; A61K 47/36; A61K 31/00
USPC ........................................................ 424/400
See application file for complete search history.

(56) References Cited

U.S. PATENT DOCUMENTS

2014/0335153 A1* 11/2014 Allen ................... A61K 9/006
514/474
2018/0000725 A1 1/2018 Lee et al.

FOREIGN PATENT DOCUMENTS

| EP | 1105108 B1 | 1/2007 |
| EP | 3513782 A1 | 7/2019 |
| WO | WO 2012/053006 A2 | 4/2012 |
| WO | WO 2016/190714 A1 | 12/2016 |

OTHER PUBLICATIONS

Visser et al., Orodispersible films in individualized pharmacotherapy: The development of a formulation for pharmacy preparations. International Journal of Pharmaceutics vol. 478, issue 1, Jan. 15, 2015, pp. 155-163. (Year: 2015).*
De Beule et al., "Pharmacology of Itraconazole." Drugs 2001; 61 Suppl. 1:27-37. (Year: 2001).*
Acevedo et al., "Thermal gelation of aqueous hydroxypropylmethylcellulose solutions with SDS and hydrophobic drug particles", *Carbohydr. Polym*, 2014; 102(1), pp. 74-79.
Chonkar et al., "Development of fast dissolving oral films containing lercanidipine HCl nanoparticles in semicrystalline polymeric matrix for enhanced dissolution and ex vivo permeation", *Eur J Pharm Biopharm.*, 2016; 103(1), pp. 179-191.
"Chemistry of Methocel—Cellulose Ethers-A Technical Review," DOW; Oct. 2013:16 pgs.
Drug Overdose Death Data | Drug Overdose | CDC Injury Center [Internet]. 2017 [cited Dec. 1, 20173]. Available from: https://www.cdc.gov/drugoverdose/data/statedeaths.html.
Egusa et al., "Oral candidosis in HIV-infected patients," *Curr HIV Res.* 2008;6(6):485-99.
Garg S, Kumar G. "Development and evaluation of a buccal bioadhesive system for smoking cessation therapy," *Pharmazie.* Apr. 2007;62(4):266-72.
Haque A, Morris ER. "Thermogelation of methylcellulose. Part I: molecular structures and processes," *Carbohydrate Polymers*, Jan. 1, 1993;22(3): 161-73.
Koyyalagunta D. Chapter 113 - Opioid Analgesics. In: Waldman SD, Bloch C drawings byJoseph I, editors. Pain Management [Internet]. Philadelphia: W.B. Saunders; 2007 [cited Dec. 1, 20175]. p. 939-64. Available from: https://www.sciencedirect.com/science/article/pii/B9780721603346501175.
Küpper et al., "J. Drugs and Drug Administration in Extreme Environments," *Journal of Travel Medicine*, Jan. 1, 2006;13(1):35-47.
Lestner et al., "Toxicodynamics of Itraconazole: Implications for Therapeutic Drug Monitoring", *Clin. Infect. Dis.*, 2009; 49(6), pp. 928-930.
Lobach et al., "Assessing the in vivo data on low/No. calorie sweeteners and the gut microbiota," *Food and Chemical Toxicology*, 2019; 124:385-399. Acesulfame potassium—an overview | ScienceDirect Topics [Internet]. [cited Jan. 1, 20187]. Available from: https://www.sciencedirect.com/topics/pharmacology-toxicology-and-pharmaceutical-science/acesulfame-potassium.
Nair et al., "In vitro techniques to evaluate buccal films", *J Control Release.*, 2013;166(1), pp. 10-21.
Naloxone: Uses, Dose & Side Effects [Internet]. Drugs.com. [cited Dec. 1, 20175]. Available from: https://www.drugs.com/naloxone.html.
Narcan (Naloxone Hydrochloride Injection): Side Effects, Interactions, Warning, Dosage & Uses [Internet]. RxList. [cited Dec. 1, 20175]. Available from: https://www.rxlist.com/narcan-side-effects-drug-center.htm.
Preis et al., "Mechanical strength test for orodispersible and buccal films", *Int. J. Pharm.*, 2014; 461(2), pp. 22-29.
Prentice and Glasmacher, "Making sense of itraconazole pharmacokinetics", *J. Antimicrob. Chemother.*, 2005;56(1), pp. 17-22.
Sangfai, et al., "Microphase Separation and Gelation of Methylcellulose in the Presence of Gallic Acid and NaCl as an In-Situ Gel-Forming Drug Delivery System", *AAPS PharmSciTech.*, 2016; 18(3), pp. 605-616.
Savjani et al. "Design and Optimization of Itraconazole Tablet Employing Solid Dispersion Approach", *Asian J. Pharm.*, 2017;11(1), pp. 192-207.

(Continued)

*Primary Examiner* — Walter E Webb
(74) *Attorney, Agent, or Firm* — Mueting Raasch Group

(57) ABSTRACT

Orodispersible films (ODFs) and methods for making the same.

20 Claims, 9 Drawing Sheets

(56) References Cited

OTHER PUBLICATIONS

Sharma et al., "Co-processing of hydroxypropyl methylcellulose (HPMC) for improved aqueous dispersibility," *Int J Pharm.* 2015;485(1-2):348-56.
Siddiqui et al., "A Novel Approach in Oral Fast Dissolving Drug Delivery System and Their Patents," *Adv Biol Res*, 2011;5(6):291-303.
Trey et al., "Delivery of Itraconazole from Extruded HPC Films", *Drug Dev. Ind. Pharm.*,2008;33(7), pp. 727-735.
XXXIV International Congress of the European Association of Poisons Centres and Clinical Toxicologists (EAPCCT) May 27-30, 2014, Brussels, Belgium. *Clinical Toxicology*, Apr. 2014;52(4):295-443. (Split into 4 documents).
Zhao et al., "Preparation of an oral thin film containing meclizine hydrochloride: In vitro and in vivo evaluation," *Intl J Pharm*, 2015;496:314-322.
Al-Gousous, "Oral Solid Dosage Form Disintegration Testing—The Forgotten Test", *J Pharm Sci.*, 2015;104(9), pp. 2664-2675.
Bagavatula et al., "Comparative Studies on Solubility and Dissolution Enhancement of Different Itraconazole Salts and Their Complexes", *Adv. Pharmacol. Pharm.*,2014;2(6), pp. 85-95.
Bala et al., "Orally dissolving strips: A new approach to oral drug delivery system", *Int. J. Pharm. Invest.*, 2013;3(2), pp. 67-76.
Borges et al., "Outlining critical quality attributes (CQAs) as guidance for the development of orodispersible films", *Pharm. Dev. Technol.*, 2017; 22(2), pp. 237-245.
Davis et al., "Engaging Law Enforcement in Overdose Reversal Initiatives: Authorization and Liability for Naloxone Administration," *American Journal of Public Health.* Aug. 2015; 105:1530-7.
Karki et al., "Thin films as an emerging platform for drug delivery", *Asian J. Pharm. Sci.*, 2016; 11(5), pp. 559-574.
Marques et al., "Simulated Biological Fluids with Possible Application in Dissolution Testing", *Dissolution Technol.*, 2011; 18(3), pp. 16-28.
Souri et al., "Validated Spectrophtometric Method for Simultaneous Determination of Buprenorphine and Naloxone in Pharmaceutical Dosage Forms, " *Iran J Pharm Res.* 2017;16(1):112-9.
Thumma et al., "Influence of plasticizers on the stability and release of a prodrug of Delta(9)-tetrahydrocannabinol incorporated in poly (ethylene oxide) matrices," *European Journal of Pharmaceutics and Biopharmaceutics*, Oct. 1, 2008;70(2):605-14.
Vazquez et al., "Optimal management of oropharyngeal and esophageal candidiasis in patients living with HIV infection," HIV Aids (Auckl). 2010;2:89-101.

* cited by examiner

THERMALLY GELLING DRUG FORMULATIONS

CROSS-REFERENCE TO RELATED APPLICATIONS

The following application claims benefit of U.S. Provisional Application No. 62/877,640, filed Jul. 23, 2019, which is hereby incorporated by reference in its entirety.

BACKGROUND

Orodispersible films (ODFs) are pharmaceutical dosage forms that are designed as a thin film having a large surface area that leads to rapid disintegration within seconds on a wet surface, such as the oral cavity. See e.g., Thakir S., Orodispersible films and their patent technology's as a novel drug delivery systems. Int. J Pharm Sci Rev Res [Internet]. 2019 September [cited 2019 Dec. 13]; 58 (1): 52-60. Advantages of this type of formulation include that the drug or other deliverable is absorbed directly into the systemic circulation, thus avoiding the hepatic $1^{st}$ pass effect. Additionally, ODFs are seen to be more convenient for patients due to their relative ease of administration. As such, this type of delivery system can lend itself to better patient compliance. If the drug is absorbed in the oral cavity then drug degradation in the gastrointestinal tract is also avoided. This type of formulation is extremely favourable for paediatric and geriatric patients that have difficulty swallowing tablets or who have a fear of chocking, patients who are unconscious, patients wherein parenteral administration brings sufficient risks (e.g., HIV patients) and/or patients suffering from dysphagia (e.g., post-stroke). Typically, the aforementioned patient groups would conventionally be given liquid or nasal spray formulations of medicines, which often have their own drawbacks (e.g. risk of microbial contamination, self-instability either over a period of months or once opened, the requirement of specialized designated devices for administration etc.).

For example, Itraconazole (ITZ) is a triazole antifungal drug that prevents the synthesis of ergosterol, the main component of fungal cell wall. ITZ is primarily used to treat candidiasis and tinea infections (See, e.g., Trey et al., (2008) Delivery of Itraconazole from Extruded HPC Films', *Drug Dev. Ind. Pharm.*, 33(7), pp. 727-735.). ITZ has a dose dependent effect for different indication, it is typically 100-200 mg; for the treatment of recurrent vulvovaginal candidiasis, but doses as low as 50 mg can be effective (See, JOINT FORMULARY COMMITTEE, 2017. Itraconazole. In: JOINT FORMULARY COMMITTEE. British National Formulary. [online]. London: BMJ Group and Pharmaceutical Press.). Physiochemically, ITZ is a Biopharmaceutical Classification System (BCS) Class II drug; exhibiting poor solubility but high permeability. Importantly due to presence the piperazine ring, the pKa of ITZ is 3.7. The drug is highly hydrophobic (log P reported to be 5.7-6.2) with no hydrogen bond donors, and very poorly water-soluble (See, Bagavatula et al., (2014) 'Comparative Studies on Solubility and Dissolution Enhancement of Different Itraconazole Salts and Their Complexes', *Adv. Pharmacol. Pharm.*, 2(6), pp. 85-95.). Its aqueous solubility is highly pH dependent, varying from 1 ng/mL at pH 7 to 4 μg/mL at pH 1. ITZ is therefore practically insoluble at physiological pH; it is very slightly soluble in alcohol (See Savjani, et al., (2017) 'Design and Optimization of Itraconazole Tablet Employing Solid Dispersion Approach', *Asian J. Pharm.*, 11(1), pp. 192-207.). However, the highly lipophilic nature of ITZ means that it readily permeates through the intestinal mucosa and the drug's absolute oral bioavailability is reported to be 55% (Saviani, supra). ITZ undergoes hepatic first pass effect. It is recommended that ITZ be taken with food (increasing oral bioavailability by 33-37%) (See, Prentice et al., (2005) 'Making sense of itraconazole pharmacokinetics', *J. Antimicrob. Chemother.*, 56(1), pp. 17-22.). ITZ is metabolised primarily by the cytochrome P450 3A4 isoenzyme system into hydroxy-itraconazole, keto-itraconazole and N-desalkyl-itraconazole; all of which are competitive inhibitors of the CYP3A4 metabolizing enzyme.

ITZ is licensed for the treatment of oral candidiasis in both HIV/other immunosuppressed patients and in non-immunosuppressed patients. ITZ is available as a capsule, oral solution, suspension and intravenous (IV) formulation. As all these require swallowing or breaking of the skin, they can complicate matters in immunosuppressed patients and patients with severe symptoms. Thus, the need for a dosage form that has none of these drawbacks can be very advantageous to patients. Considering ITZ's physiochemical properties such as limited solubility and its subjection to hepatic 1st pass metabolism, an ODF comprising itraconazole would be highly desirable.

As another example, naloxone is an inverse opioid agonist which binds with high affinity to the μ-opioid receptor and to a lesser extent to the kappa and delta opioid receptors. When the drug binds, it replaces the offending opioid at the active site and elicits the opposite pharmaceutical effects. (See, Koyyalagunta D. chapter 113—Opioid Analgesics. In: Waldman S D, Bloch C drawings by Joseph I, editors. Pain Management [Internet]. Philadelphia: W.B. Saunders; 2007 [cited 2017 Dec. 15]. p. 939-64.) If given in time, naloxone reverses respiratory depression caused by an opioid overdose and can be lifesaving. In the United States 64000 people died from drug overdoses in 2016, around 53000 of which were opioid related, making opioids the leading cause of death in people under the age of 50. Furthermore, the death toll in 2016 was 22% higher than the previous year. The increase was in part due the potent opioid fentanyl becoming more widely available. Deaths from fentanyl have increased by 540% in the past 3 years. (See, e.g., Drug Overdose Death Data|Drug Overdose|CDC Injury Center [Internet]. 2017 [cited 2017 Dec. 13]. Available from: https://www.cdc.gov/drugoverdose/data/statedeaths.html) Public health campaigns have focused on getting naloxone into the hands of as many members of the public as possible, with focus on the family and friends of users. (See, Davis et al., Engaging Law Enforcement in Overdose Reversal Initiatives: Authorization and Liability for Naloxone Administration. American Journal of Public Health. 2015 August; 105:1530-7.) Accordingly, the need for an easy to use and inexpensive naloxone delivery system such as that disclosed herein, is more important than ever.

Currently naloxone is licensed as IV, S/C and IM formulation in both the EU and US. It is also approved as a nasal spray in the US. (See, Naloxone: Uses, Dose & Side Effects [Internet]. Drugs.com. [cited 2017 Dec. 15]. Available from: https://www.drugs.com/naloxone.html) All the current delivery methods require a device for administration. This complicates their use for the everyday user. Coupled to this naloxone's half-life is short, at around 30 minutes. (See, Narcan (Naloxone Hydrochloride Injection): Side Effects, Interactions, Warning, Dosage & Uses [Internet]. RxList. [cited 2017 Dec. 15]. Available from: https://www.rxlist.com/narcan-side-effects-drug-center.htm) As a result, re-dosing is often required. naloxone's viability can only be ensured if it is carried by first responders and members of the public. As such, a delivery method, such as that disclosed herein, which is compact and easy to carry presents a huge advantage.

The current most prominent method used in the formulation and manufacture of orodispersible thin films is solvent casting. This generally involves creating a casting solution of an aqueous based polymer with a uniformly dispersed active pharmaceutical ingredient (API). The solvent casting solution generally de-gassed, is applied to a casting surface, before drying and cutting to the appropriate size before packaging. See, e.g., Morales J, McConville J. Manufacture and characterisation of mucoadhesive buccal films. Eur J Pharm Biopharm [internet]. 2011 February [cited 2019 Nov. 3]; 77(2): 187-99.

However, the solvent casting method for thin film production has limitations, including: difficulty and expense related to scaling up for industrial manufacture, long drying times, lack of drug uniformity which could lead to unsafe dosing, and variable storage conditions for the finished product. (See, e.g., U.S. Pat. No. 7,425,292 issued Sep. 16, 2008.) For example, the problems associated with long drying times at room temperature (RT) have led to the use of ovens for drying; in some cases, a hot forced-air oven. This subjects the film to stress, and can cause a rippling effect which can lead to clumping and non-uniform drug distribution. The use of ovens can also result in degradation of the API. Moreover, the hygroscopic nature of films can cause issues for storage and stability. See e.g., Karki, S. et al., Thin films as an emerging platform for drug delivery. Asian J. Pharm. Sci. [Internet]. 2016 June [cited 2019 Dec. 13]; 11(5):559-74.

Furthermore, many APIs and or desirable additives are hydrophobic. However, the incorporation of a uniform distribution of a hydrophobic agent into ODFs has proven to be extremely difficult.

Accordingly, novel ODFs and methods for forming the same that overcome these limitations are greatly desired.

SUMMARY

The present disclosure provides orodispersible films (ODFs) and methods for making the same. According to an embodiment, the ODFs are formed using a solvent casting technique wherein a mixture comprising a thermoresponsive polymer, an active pharmaceutical ingredient (API) and any optional excipients or other ingredients are cast at a temperature at or above the thermal gelation point of the mixture to form a stable gel, the solvent in the gel is then evaporated to produce a thin film.

DETAILED DESCRIPTION

Figure 1:
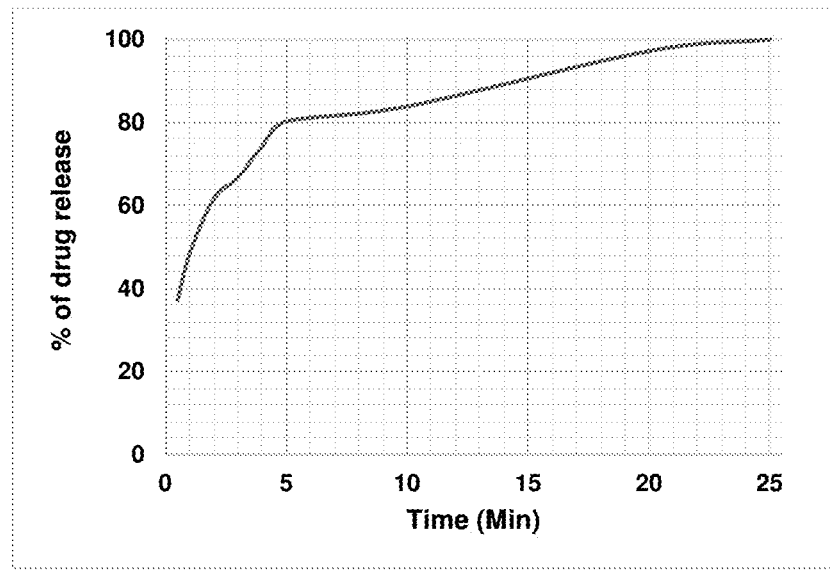
FIG. 1 is a graph showing drug release of an ODF according to the present disclosure in saliva media.

According to an embodiment the present disclosure provides thermally gelling drug formulations and methods and uses therefore. According to an embodiment, the formulation takes the form of a thin film which may be an orodispersible film (ODF), which may be a rapid, slow, sustained, multi-stage, (or a combination thereof) release thin film containing a drug or other deliverable (also referred to herein as an active pharmaceutical ingredient, API). The ODF may also contain a variety of excipients including, but not limited to polymers, release rate controlling agents, plasticizers, sweeteners, saliva stimulating agents, taste masking agents, flavorings, colorants, preservatives, and the like. For ease of discussion, the API(s) and excipients are collectively referred to herein as "ingredients".

According to an embodiment, the ODF may be formed using a novel solvent casting technique. In standard solvent casting methods, a polymer is solubilized in a solvent with an API and any desired excipients and the resulting liquid is poured (or cast) onto a substrate and then rapidly dried to form a film. Unfortunately, this technique can result in uneven distribution of the API and excipients. In order to address the issue of uneven distribution, previously described solvent casting methods have focused on altering the drying conditions by increasing temperatures to shorter drying times and the use of non-standard ovens or other custom or expensive drying equipment and other methodologies to quickly and/or more evenly evaporate the solvent. However, higher drying temperatures bring their own set of issues such as rippling and other surface defects. Moreover, high drying temperatures and/or the incorporation of other solvents (e.g. ethanol) can be detrimental with the inclusion of certain APIs including various temperature-sensitive biologicals or pharmaceuticals.

Accordingly, the present disclosure provides a novel solvent casting technique to produce a uniform distribution of ingredients while avoiding high temperatures, non-standard ovens or other custom or expensive drying equipment and other methodologies to quickly and/or more evenly evaporate the solvent. In general, the term "uniform distribution" is intended to mean a high content uniformity of ingredients within a thin film, as opposed to a film displaying overly heterogeneously distributed ingredients. However, it will be appreciated that what is considered a uniform distribution may depend on the allowed variability tolerance of a specific active ingredient. According some embodiments, a uniform distribution may mean that there is less than 10% variability of ingredients distributed within a film. According to still other embodiments, a uniform distribution may mean that there is less than 5% variability of ingredients distributed within a film.

Briefly, while previously described solvent casting techniques go from a liquid state to a solid film state as quickly as possible in order to "lock" the various ingredients into position and produce films with a uniform distribution of ingredients, the present disclosure utilizes an intermediate semi-solid gel state to lock the ingredients into place, allowing for a gentler transition into the solid film state, making the process additionally appropriate for thermally labile drugs as well as biologics.

According to various embodiments, a hydrophilic polymer is mixed with the desired ingredients (i.e., one or more APIs and any desired excipients) in a solvent. The mixture is then cast onto a form (or substrate) at or above the thermal gelation point of the mixture to form a stable gel. Thermal gelation is a phenomenon that occurs, for example, when a polymer (or mixture containing a polymer) is dissolved in an aqueous media and heated to its "gelation temperature;" causing a change in viscosity and physical properties. In solution and at low temperatures, the molecules in the polymer are hydrated and experience little polymer-to-polymer interaction other than simple polymer chain entanglement. For example, as the temperature of the cellulosic polymer solution is raised, the polymeric chains start to lose their hydration and the solution viscosity is affected. When the thermal gelation temperature (TGel) is achieved, adequate dehydration of the polymer arises to cause a polymer-to-polymer interaction, and the solution begins to gel (See, e.g., Acevedo et al., (2014) 'Thermal gelation of aqueous hydroxypropylmethylcellulose solutions with SDS and hydrophobic drug particles', *Carbohydr. Polym.*, 102(1), pp. 74-79).

For the purposes of the present disclosure the term "gel" is defined as a substantially dilute cross-linked semi-solid system, which exhibits no flow when in the steady-state but has viscoelastic properties that are dependent on the polymer type and concentration used. The term "gel" is presented in contrast to the term "thin film" which is intended to mean a thin self-supporting solid material of uniform distribution. Notably, according to this disclosure, the ingredients are locked into a uniform distribution in the gel before formation of a thin film. The gel is then dehydrated to produce a film, which can then be cut into any desirable shape or size to produce an ODF or extended release film. According to an embodiment, an ODF may be less than 100 µm thick, with, for example, dimensions similar to a postage stamp (20×30 mm$^2$).

For the purposes of the present disclosure, the term "stable" with reference to a "stable gel" is intended to mean that all or substantially all of the mixture that was cast onto the substrate rapidly (i.e. in less than 5 minutes, preferably less than 2 minutes and even more preferably less than 1 minute) forms into and is maintained as a gel (as opposed to a liquid or a film), thus distinguishing the present methodology from previously described methods wherein a mixture is poured or cast onto a substrate and immediately dehydrated to form a film Because the ingredients are locked into a stable formation in the gel, the present disclosure allows for a slow evaporation of the solvent. Specifically, unlike the evaporation steps in previously described methods which take place on the order of a several minutes before the conventional casting solution becomes viscous enough to stop the movement of ingredients, the presently described evaporation step can take place much more slowly over the course of minutes, hours, or even days. Moreover, as stated above, the evaporation step can take place under controlled conditions, including but not limited to, temperature, pH, and solvent type, which are suitable to maintain viability for biological ingredients and/or activity for labile pharmaceutical ingredients.

Moreover, it should be understood that because the ingredients are locked into place in the viscoelastic gel state, additional or alternative manipulation of the gels may be performed prior to casting. For example, the gels could be placed under shear force for extrusion into films or other forms.

The polymer may be any suitable polymer or polymer mixture subject to thermal gelation. Suitable thermoresponsive hydrogels may include but are not limited to: copolymeric hydrogel mixtures (e.g. poly(DL-lactide-co-glycolide) and poly(DL-lactide-co-E-caprolactone)), gelling mixtures (e.g. N-[(2-hydroxy-3-methyltrimethylammonium)propyl], chitosan chloride, and poly (ethylene glycol)), glycosaminoglycans (e.g. chrondroitins, heparin, hyaluronic acid, keratin), micellar gelling systems (e.g. poly(N-isopropylacrylamide)-block-poly(sulfobetaine methacrylate) (PNIPAAm-b-PSBMA) block, organogels (e.g. 4-tertbutyl-1-aryl cyclohecanol derivatives, Boc-Ala(1)-Aib(2)-ß-Ala (3)-OMe, fatty acids and n-alkanes, N-lauroyl-L-lysine ethylester, poly(ethylene glycol), polycarbonates, polyesters and poly(alkylene)), phycocolloids (e.g. agars, alginates, carageenans), polyacrylic type gels (e.g., poly-(N-isopropyl acrylamide), polyacrylic and polymethacrylic acid and derivatives), polyesters (e.g. PLA, PLGA), polysaccharide type gels (e.g. cellulose and derivatives, chitosan and derivatives, gellan gum, glucomannan, modified dextrans, starch and derivatives, xanthan gum, xyloglucans), protein type gels (e.g. albumen, collagen, fibrin, pectin, silk fibroin), thermoresponsive terpolymers complexes (e.g. N-isopropylacrylamide, hydroxyethyl methacrylate, and 2-acrylamido-2-methylpropane sulfonic acid), thermoresponsive vitrimers and composites (e.g. polyurethane-forming components with functional groups), triblock polymer systems (e.g. poly(DL-lactide)-block-poly(ethylene glycol)-block-poly (DL-lactide), poloxamers), and combinations or ingredients thereof.

Suitable APIs include, but are not limited to, poorly soluble drugs such as itraconazole (ITZ), drugs with short half-lives, and drugs which typically require devices for delivery (e.g. naloxone). Other suitable APIs include, but are not limited to, ace-inhibitors, antacids, anti-Alzheimer's agents, antianginal drugs, anti-arrhythmias, anti-asthmatics, anti-cholesterolemics, antibiotics, analgesics, anesthetics, anti-anxiety agents, anti-coagulants, anti-convulsants, anti-depressants, anti-diabetic agents, anti-diarrhea preparations, antidotes, anti-emetics, anti-histamines, anti-hypertensive drugs, anti-inflammatory agents, anti-lipid agents, anti-manics, anti-nauseants, anti-obesity drugs, anti-psychotics, anti-pyretics, anti-stroke agents, anti-thrombotic drugs, anti-thyroid preparations, anti-tumor drugs, anti-viral agents, acne drugs, alkaloids, amino acid preparations, anti-spasmodics, anti-tussives, anti-uricemic drugs, anti-ulcer agents, anti-viral drugs, anabolic preparations, systemic and non-systemic anti-infective agents, anti-neoplastics, anti-parkinsonian agents, anti-rheumatic agents, appetite stimulants, appetite suppressants, biological response modifiers, blood modifiers, bone metabolism regulators, breath fresheners, bronchodilators, ca-antagonists, cardiovascular agents, central nervous system stimulates, cholinesterase inhibitors, contraceptives, coronary dilators, cerebral dilators, cough suppressants, decongestants, dietary supplements, DNA and genetic modifying drugs, diuretics, dopamine receptor agonists, endometriosis management agents, enzymes, erectile dysfunction therapies, erythropoietic drugs, expectorants, fertility agents, gastrointestinal agents, H-antagonists, homeopathic remedies, hormones, hypnotics, hypercalcemia and hypocalcemia management agents, hyper and hypoglycemic agents, immunomodulators, immunosuppressives, laxatives, migraine preparations/treatments, motion sickness treatments, mucolytics, muscle relaxants, neuromuscular drugs, obesity management agents, osteoporosis preparations, oxytocics, parasympatholytics, parasympathomimetics, peripheral vasodilators prostaglandins, psychotherapeutic agents, psycho-tropics, respiratory agents, sedatives, smoking cessation aids, stimulants, sympatholytics, thyroid and anti-thyroid preparations, tranquilizers, tremor preparations, urinary tract agents, uterine relaxants, vasoconstrictors, vasodilators, vitamins, and combinations or ingredients thereof.

Suitable biologicals include, but are not limited to, allergenics and extracts, anesthetics, antibiotics, anti-inflammatory compounds, antivirals, biosimilars, cytokines, cytostatic and cytotoxic drugs and other anti-cancer agents, diagnostic agents, enzymes, growth factors, hormones, imaging agents, immunosuppressants and immunostimulators, monoclonal antibodies, mucolytic and virolytic compounds, toxoids, vaccines, venoms and venom proteins, or other biologically active agents or combinations and ingredients thereof.

Suitable excipients include, but are not limited to plasticizers, sweeteners, saliva stimulating agents, taste masking agents, flavourings, colourants, preservatives, combinations, and ingredients thereof.

Suitable solvents are often, but not limited to aqueous based systems, examples include: water, buffer, suitable organic solvents (e.g. ethanol), or combinations thereof.

Importantly, the thermal gelation temperature can be affected by the ingredients that are added to the polymer mixture. For example, hydrophobic ingredients may increase thermal gelation temperature. Accordingly, it may be necessary to increase the casting temperature to a temperature above or substantially higher than the gelation temperature of the polymer mixture as a whole. However, temperatures which are too high can result in the formation of air bubbles (in systems that have not been de-gassed) leading to an inconsistent texture. Therefore, it may be desirable to cast the films at a temperature which is higher than the gelation temperature of the mixture, but which limits or eliminates bubble formation. Moreover, as stated above, high temperatures may be detrimental for certain ingredients. In this case, it may be desirable to include a gelling aid to reduce the thermal gelation temperature and enable the inclusion of temperature-sensitive ingredients.

Suitable gelling aids may include, but are not limited to compounds that contain "salt-out-anions" such as 2-(2-methoxyethoxy)ethylsulfate, 2-carboxybenzoate, Acetate, Aluminumtetrachlorate, Aspartate, Benzoate, bis(trifluoromethyl)azanide, bis(trifluoromethylsulfonyl)imide, bis(trifluoromethylsulfonyl)methane, Bromide, Carbonate, Chloride, Choline, Citrate, Decanoate, Dibutylphosphate, Dicyanamide, Diethylphosphate, Dimethylphosphate, Dodecylbenzenesulfonate, Ethoxyethylsulfate, Ethylsulfate, Fluoride, Fumerate, Guanidinium, Hexafluorophosphate, Hydrogen carbonate, Hydrogen phosphate, Hydrogensulfate, Iodide, Imadozolium, Lactate, Malate, Maleate, Methanoate, Methanesulfonate, Methoxyethylsulfate, Methylphosphate, Methylsulfate, Morpholinium, Nitrate, Nitrite, Octylsulfate, Oxalate, Perchlorate, Phosphate, Phosphonium, Picrate, Piperidinium, Propionate, Pyridinium, Pyrolidinium, Salicylate, Succinate, Sulfate, Sulfonate, Tetracyanoborate, Tetrafluoroborate, Tetrafluorophosphate, Thiocyanate, Trichloroacetate, Toluene-4-sulfonate, Tricyanomethanide, or Tri-fluoro-methane, Tri-fluoro-methane-sulfonate and the like). Additionally gelling aids may include, but are not limited to compounds that contain to "salt-out-cations" such as Aluminum, Ammonium, Aminopyridines, Barium, Beryllium, Calcium, Cobalt, Copper, Iron, Lithium, Magnesium, Manganese, Nickel, Potassium, Sodium, Tetraethyl Ammonium, Tetramethyl Ammonium, Zinc salts and the like. For the purposes of the present disclosure, the terms "salt-out anion" and "salt-out cation" are intended to mean either an anion or cation that has a strong affinity for water and hydration, respectively. Other gelling aids may include agents having a high affinity for water that can further promote gelation of polymers. Moreover, a combination of gelling aids may be used.

According to some embodiments, it may be difficult to incorporate hydrophobic ingredients into the thin film. Accordingly, it may be desirable to add a pre-dispersed mixture of the hydrophobic material. For example, in order to add the hydrophobic ingredient ethyl cellulose (EC) to a casting solution of hypromellose a pseudolatex dispersion of EC can be mixed into the liquid phase prior to gelation.

According to some embodiments, the film may be formulated to provide single or multi-stage delivery of the API. For example, the thin film could be designed to provide slow release, rapid release, sustained release, multi-stage release, or a combination thereof. According to an embodiment, multi-stage release may take the form of an initial burst release upon contact with the mucosa followed by a period of sustained release. As described in greater detail in the Examples section below, an API that has been sprayed onto the surface of a film is typically released by the film much faster than API that have been incorporated into the gel during gel formation. Accordingly, the present disclosure contemplates an ODF comprising one or more ingredients that are sprayed or otherwise applied to the surface of the ODF after formation of the film.

Similarly, the ODF may be modified after formation of the film to include surface coating, annealing, heat modification, radiation exposure, ionization, or any chemical surface modification.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

EXAMPLES

Examples 1-8—Itraconazole-Containing ODFs (Table 1)

ITZ was added to 150 mL of deionised water with mixing (30 mins), 15 mins sonication, followed by 5 mins further mixing. Acesulfame potassium (AceK) up to 0.3% w/w and Polyethylene oxide (PEO) or Polyethylene Glycol (PEG) 400 (20-30% w/w) was added and mixed until completely dissolved. Citric acid was added as a potential saliva stimulating agent (1-3% w/w). The solution was then heated to 60° C. and HPMC E4 (2% w/w) was gradually added and mixed for 40 mins, until the HPMC had fully dispersed in the mixture. The mixture was then cooled in an ice bath for 20 mins until all the HPMC was dissolved.

Following 24 hours refrigeration the mixture was placed in a vacuum chamber to degas. The casting mixture was cast onto preheated metal backing trays in an oven at 80° C. (>TGel) overnight until dry. The resulting films were cut to 6 cm2 (20×30 mm2).

The various formulations tested are shown in Table 1. All formulations shown in Table 1 include 2% w/v of HPMC but vary in the pharmaceutical ingredient that constitute the formulation and the amount it makes up. Each pharmaceutical ingredient is quoted as a percentage of the weight of dry HPMC powder used.

TABLE 1

Film compositions.

| ID | PEG 400 | Ace K | Citric acid | PEO |
|----|---------|-------|-------------|-----|
| F1 | — | — | — | — |
| F2 | 20 | — | — | — |
| F3 | 20 | 15 | 150 | — |
| F4 | 20 | 15 | — | — |
| F5 | 30 | 15 | 50 | — |
| F6 | 20 | 15 | 50 | — |
| F7 | — | 15 | — | 20 |
| F8 | — | 15 | 50 | 20 |

Folding endurance was carried out using an established method by continually folding the F7 ODFs along the same place until the film breaks. (See, Chonkar et al., (2016) Development of fast dissolving oral films containing lercanidipine HCl nanoparticles in semicrystalline polymeric matrix for enhanced dissolution and ex vivo permeation', *Eur J Pharm Biopharm.*, 103(1), pp. 179-191.). The folding endurance exceeded 300 folds for each of the films tested. Thickness was tested by measuring 4 different points on five F7 films, using an electronic micrometre. The thickness of the ITZ ODF was recorded to be 58±13 µm (mean±SD).

Load, elongation. stress and tensile strangth were evaluated on six different F7 films using a Chatillon TCD200 motorised force tester (Chatilon, Greenwitch, USA) (Table 2). Strength and elongation readings measure the maximal load a film can withstand and the amount of elongation that occurs. All films surpassed a threshold level of 24 N, with some exceeding 30 N. The extent of elongation varied between the films tested, ranging from 2.5 mm to 4.4 mm.

TABLE 2

Strenth and elongation readings of films

| Film | Load (N) | Elongation (mm) | Stress (%) | Tensile Strength (N/mm$^2$) |
|------|----------|-----------------|------------|------------------------------|
| 1 | 24.3 | 3.67 | 18.3 | 20.9 |
| 2 | 24.6 | 3.75 | 18.8 | 21.2 |
| 3 | 29.8 | 2.99 | 14.91 | 25.7 |
| 4 | 26.5 | 2.37 | 11.82 | 22.8 |
| 5 | 32.4 | 4.28 | 21.35 | 27.9 |
| 6 | 32.2 | 4.02 | 20.15 | 27.8 |
| Average | 28.3 | 3.5 | 17.6 | 24.4 |

F7 ODFs were cut to 1 cm×1.5 cm in size, and their weights were recorded. Films (n=10) were completely dissolved in deionised water, 1 mL of the resultant solution was analysed using UV spectroscopy at 262 nm to measure drug content uniformity. The drug content of a 1.5 cm$^2$ film (n=10) was 96±30 µg (mean±SD) and the average weight was 7.2±1.3 mg (mean±SD).

To test disintegration time, ODFs were placed in a beaker containing 10 ml of saliva media at 37° C. and was gently swirled. Disintegration time was considered the time taken for the ODF to start disintegrating (Chonkar et al., supra). Disintegration in this test was defined as the time the film lost its structural integrity and shape, as well as starts to dissolve. The test was carried out in triplicate and the average value was reported. The disintegration time for the ITZ ODFs was 38±4.6 seconds.

To test drug release in saliva media, a modified USP 2 paddle method was used, each vessel contained containing sodium chloride (3.2 g), potassium phosphate monobasic (76 mg) and sodium phosphate dibasic (952 mg) in 400 mL of deionised water adjusted to pH 6.8. The media was maintained at 37±1° C. and was stirred at 75±2 rpm. One ITZ ODF (2 cm×3 cm) was placed in each of 2 baskets which were placed in the bottom of each dissolution cup (800 mL). Samples of 1 ml were withdrawn at 30 s, then every minute during 5 min and then at 10, 20 and 25 mins. Fresh medium was replaced when extracting each sample for testing. Samples were analysed in triplicates using UV to determine drug release. Burst release was observed for all films; within 2 minutes, 60% of the drug was released, with 100% liberated within 25 mins. The initial average release rate of the drug was calculated to be 86 µg/min. For all films tested, no differences in the amount released between 2 and 3 minutes was observed. Thereafter, all films gradually released the remaining drug over 20 minutes. The average dissolution profile of three runs carried out can be seen in FIG. 1.

Figure 2:
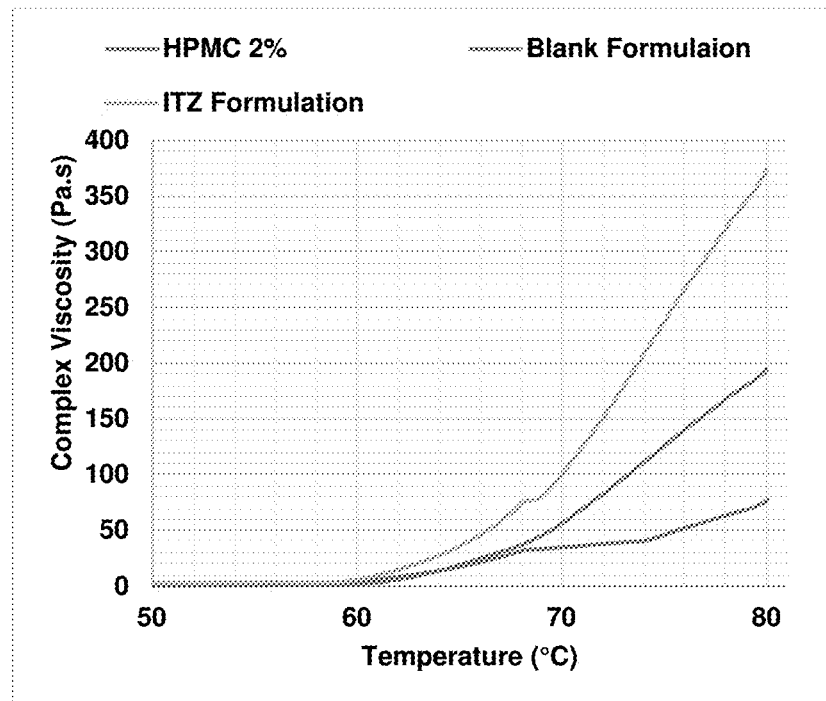
FIG. 2 shows the results of rheological analysis carried out on a casting mixture of an itraconazole-containing ODF according to the present disclosure, pure 2% HPMC, and a blank ODF formulation without the ITZ added to determine the gelation temperature, how the viscosity changes as temperature increases, and how sheer force affects the behavior of the gel

Rheological analysis was carried out on formulation F7 casting mixture, pure 2% HPMC, and a blank F7 formulation without the ITZ added to determine the gelation temperature, how the viscosity changes as temperature increases, and how sheer force affects the behavior of the gel (FIG. 2). HPMC 2% alone had a gelation temperature of 64.6° C., blank F7 formulation (2% HPMC, 0.3% ACE K and 20% PEO) had a gelation temperature of 61.5° C., while the formulation with F7 ITZ formulation had a gelation temperature of 69.1° C.

Figure 3:
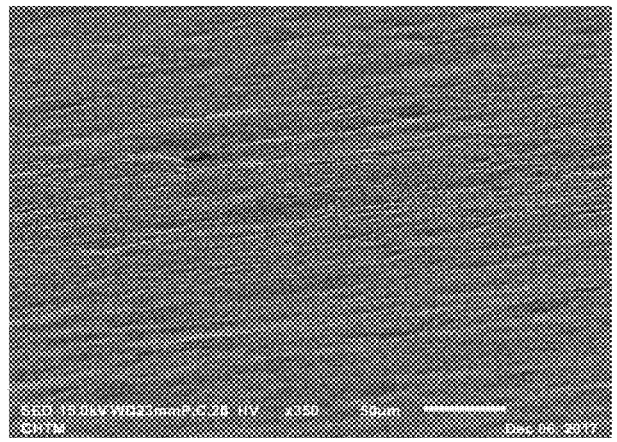
FIG. 3 is a scanning electron microscopy (SEM) image of the surface morphology of a ODF formed according to the present disclosure.
Figure 4:
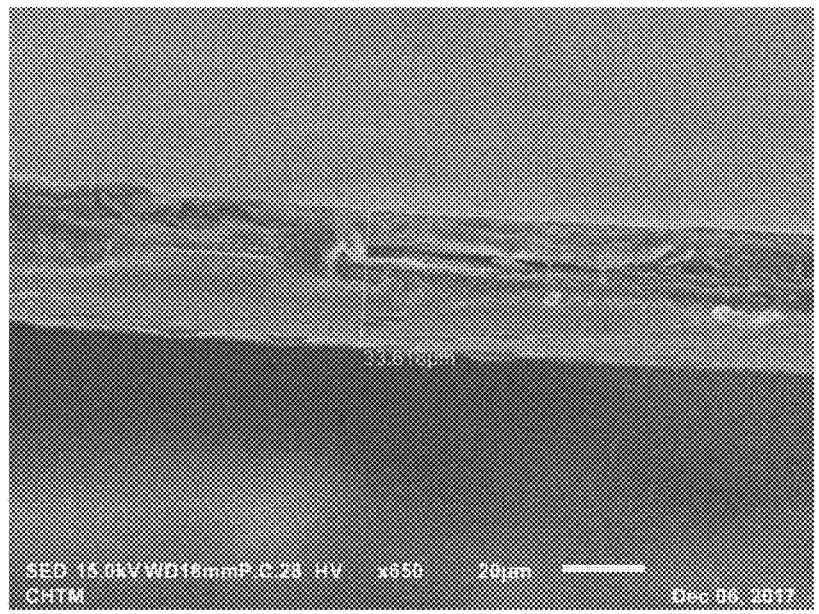
FIG. 4 is an SEM image showing the supplementary thickness of an ODF formed according to the present disclosure.
Figure 5:
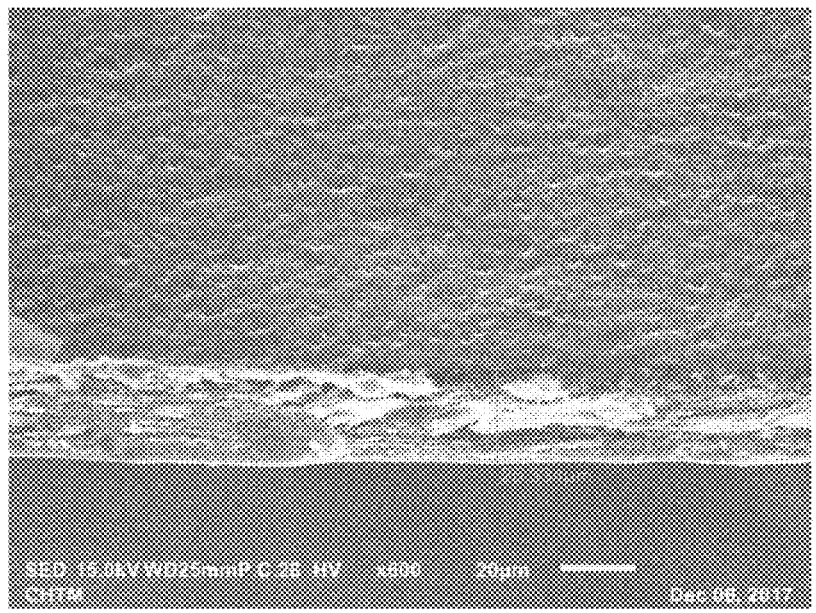
FIG. 5 is an SEM image also showing the supplementary thickness of the ODF of FIG. 4.

Surface morphology (FIG. 3) and supplementary thickness (FIGS. 4 and 5) testing was carried out by scanning electron microscopy. As shown, the film's surface is relatively uniform with no obviously "rough" areas apparent. FIGS. 4 and 5 show slight variation in thickness between 25.3 μm and 33.6 μm.

Examples 9-12—Ibuprofen or Itraconzole-Containing ODFs

Four samples were tested for viscosity and thermal gelation points. The samples were prepared as follows: Methocel E50 (6 g) was dissolved with an electric stirrer in 60 g of water at 85° C., until dispersed. This mixture was then cooled to <30° C., with the remaining 40 g of ice water and mixed for a further 45 minutes, before being covered and refrigerated overnight. The drug was then added with electronic mixing to ensure an even dispersion.

The following samples were made:

A1—6% HPMC

A2 6% HPMC+120 mg Ibuprofen

A3 6% HPMC+400 mg Ibuprofen

A4 6% HPMC+120 mg Itraconazole

Figure 6:
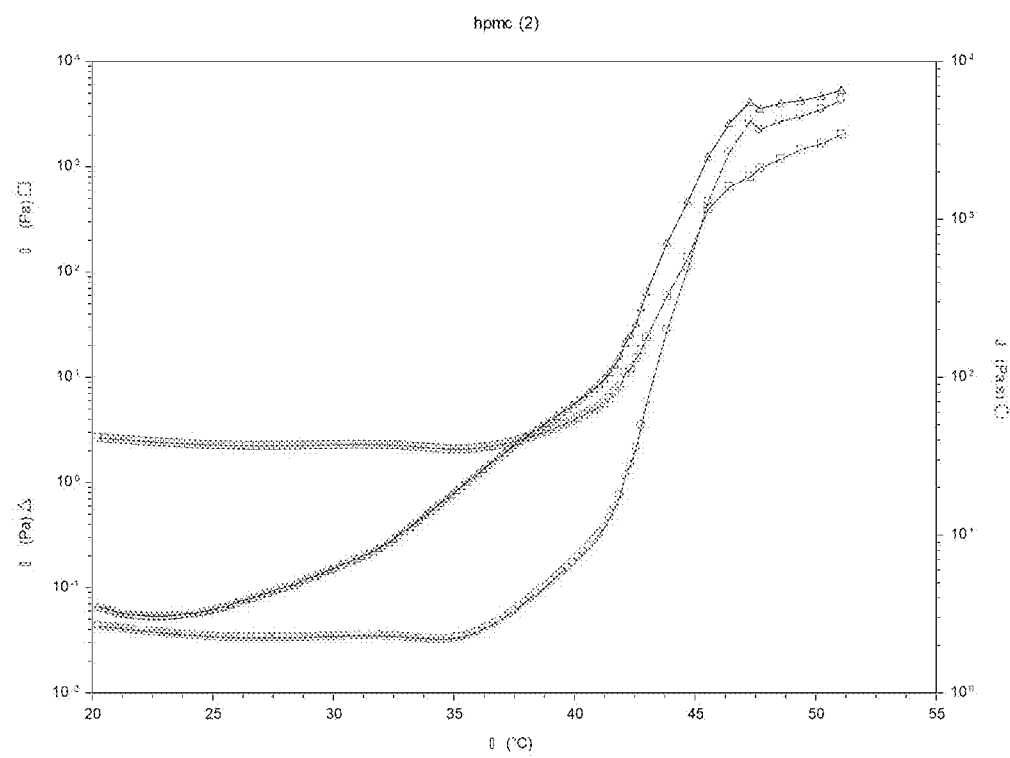
FIG. 6 is a graph showing the thermal gelation temperature of HPMC alone.
Figure 7:
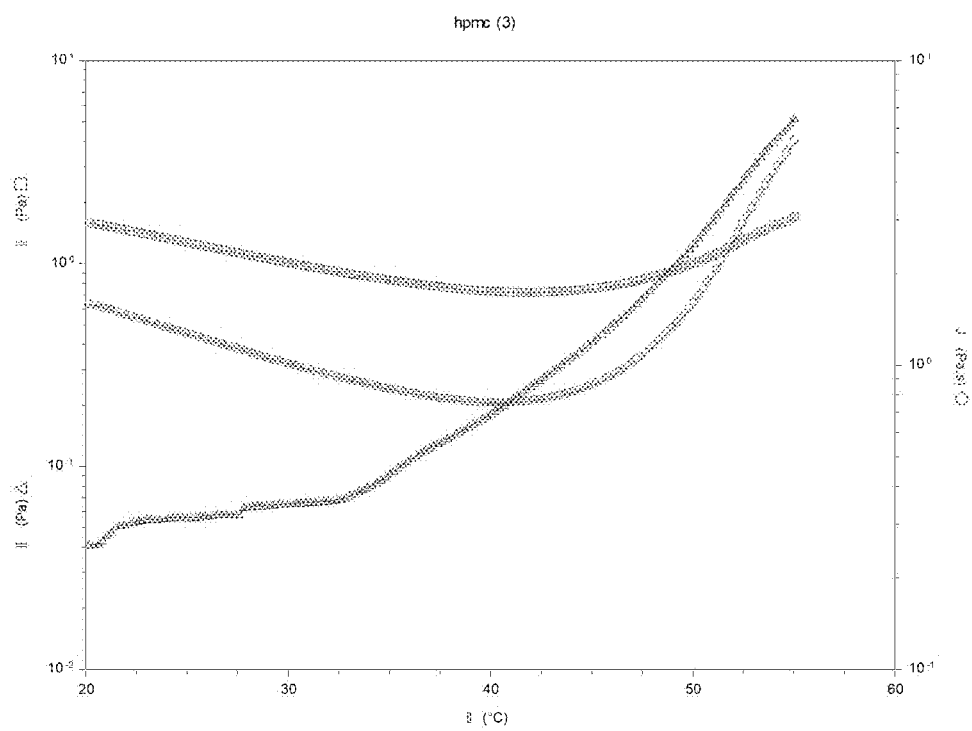
FIG. 7 is a graph showing the thermal gelation temperature of HPMC+120 mg ibuprofen.
Figure 8:
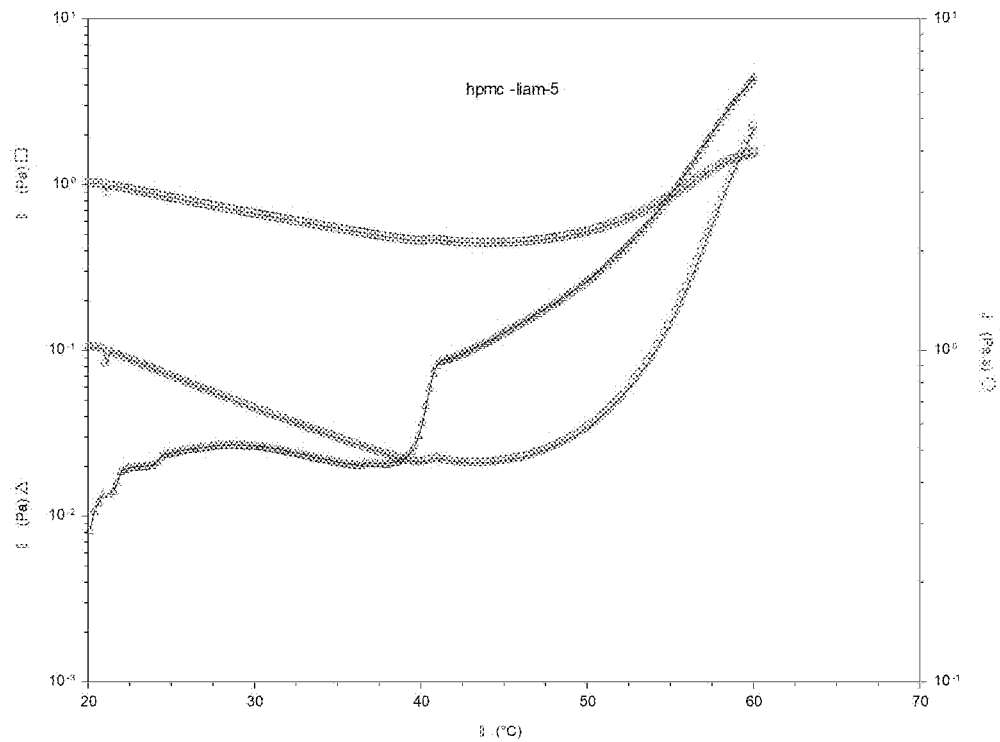
FIG. 8 is a graph showing the thermal gelation temperature of HPMC+400 mg ibuprofen.
Figure 9:
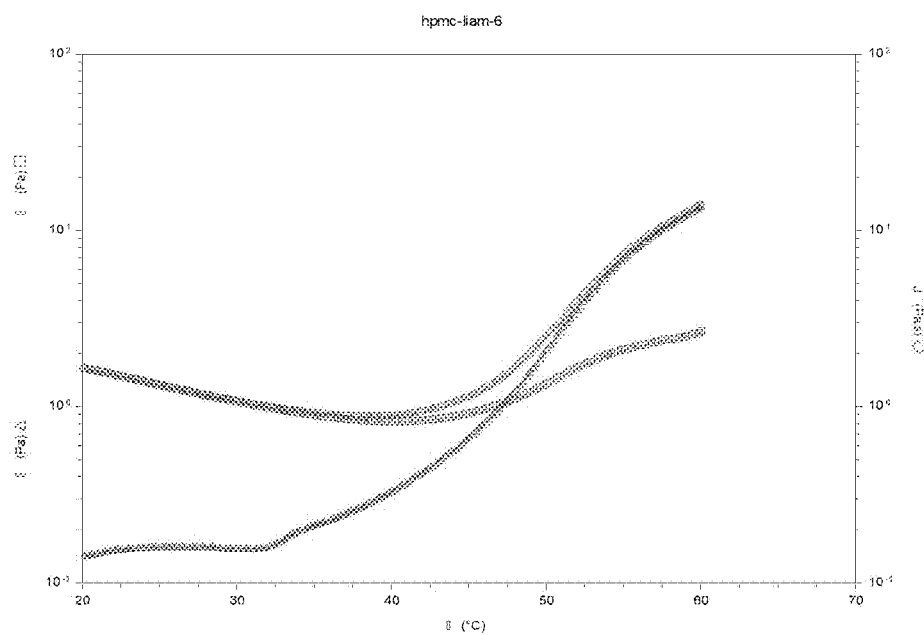
FIG. 9 is a graph showing the thermal gelation temperature of HPMC+itraconazole.

FIGS. 6-9 show the thermal gelation temperatures of the various samples (as determined using a rheometer). HPMC (A1) alone had a thermal gelation temperature of 32° C. (FIG. 6). HPMC+120 mg ibuprofen (A2) had a thermal gelation temperature of 36° C. (FIG. 7). HPMC+400 mg ibuprofen (A3) had a thermal gelation temperature of 38° C. (FIG. 8). HPMC+itraconazole (A4) had a thermal gelation temperature of 47.5° C. (FIG. 9).

Examples 13-15 Casting Temperature

Figures 10, 11:
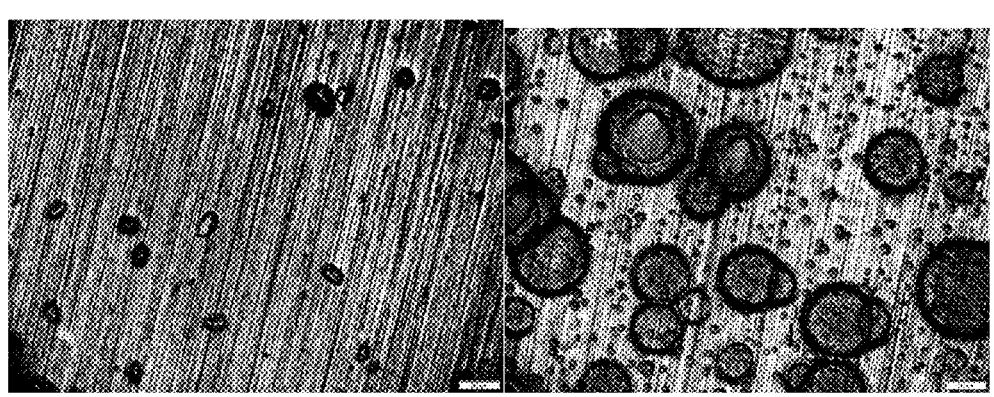
FIG. 10 is an image of an itraconzole-containing ODF according to the present disclosure cast at room temperature (22° C.).
FIG. 11 is an image of an itraconzole-containing ODF according to the present disclosure cast at 80° C.
Figure 12:
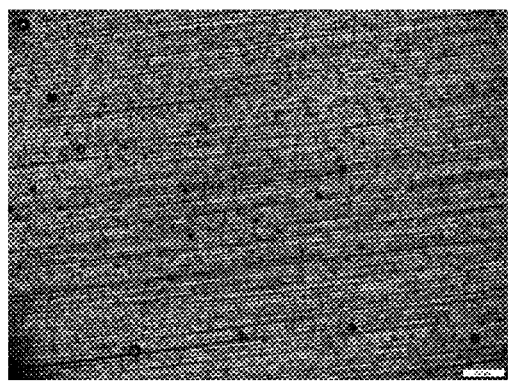
FIG. 12 is an image of an itraconzole-containing ODF according to the present disclosure cast at 70° C.

FIGS. 10-12 show A4 itraconazole containing films cast at different temperatures in triplicate (TG1-3 are above TGel, RT1-3 are below TGel). The oval shapes in the (below TGel) room temperature (RT) 22° C. cast (FIG. 10) were deemed to be drug aggregation. However, there is a distinct lack of the circular formations that are so abundant in the 80° C. cast (FIG. 11). These are believed to be air bubbles generated from the dearation of water at the higher temperature. However, in the 70° C. cast (FIG. 12) there is no drug aggregation present and very few air bubbles.

Overall the 22° C. film was slightly thinner than the thermally gelled (TG) film and had less uniformity with points that were thicker than any point on the TG film (Table 3). Areas attributed to drug aggregation were observed as visible as white spots on the 22° C. cast films.

TABLE 3

Physical characteristics of the films

| Film | Thickness 1 (μm) | Thickness 2 (μm) | Thickness 3 (μm) | Average (μm) |
|---|---|---|---|---|
| RT 1 | 0.047 | 0.041 | 0.050 | 0.046 |
| RT 2 | 0.051 | 0.044 | 0.047 | 0.047 |
| RT 3 | 0.047 | 0.053 | 0.046 | 0.049 |
| Average | | | | 0.047 |
| TG 1 | 0.031 | 0.076 | 0.037 | 0.048 |
| TG 2 | 0.065 | 0.079 | 0.040 | 0.061 |
| TG 3 | 0.039 | 0.061 | 0.065 | 0.055 |
| Average | | | | 0.055 |

The tensile strength and percentage elongation of the films was tested (Table 4). Overall, the films produced above the thermal gelation had a slightly lower breaking force than the RT films, but the % elongation before break was slightly higher.

TABLE 4

Tensile testing of films following casting.

| Film | Tensile Strength ($N/m^2$) | Percentage Elongation (%) |
|---|---|---|
| TG 1 | 14930 | 5.050 |
| TG 2 | 14960 | 5.159 |
| TG 3 | 14480 | 5.846 |
| Average | 14790 | 5.352 |
| RT 1 | 17140 | 5.898 |
| RT 2 | 18010 | 5.481 |
| RT 3 | 15480 | 3.345 |
| Average | 16877 | 4.908 |

The average disintegration times for both films was less than 30 seconds, complying with the European Pharmacopeia specification of 3 minutes (Table 5).

TABLE 5

Disintigration Testing

| Film | Film mass (mg) | Disintegration Time (s) |
|---|---|---|
| TG1 | 0.0204 | 22.08 |
| TG2 | 0.0174 | 25.29 |
| TG3 | 0.0210 | 24.02 |
| TG4 | 0.0212 | 30.42 |
| Average | 0.0200 | 25.45 |
| RT1 | 0.0214 | 32.19 |
| RT2 | 0.0208 | 19.35 |
| RT3 | 0.0195 | 28.74 |
| RT4 | 0.0199 | 33.61 |
| Average | 0.0204 | 28.47 |

Example 16—2-Step Release Naloxone-Containing ODFs

Naloxone-containing ODFs were formed by separately first dispersing 2 g Methocel E4M in 60 g hot DI water (>80 degrees C.), before adding 40 g ice and allowing the HPMC to dissolve. Naloxone (10 mg), PEO N80 (0.4 g), citric acid (6 mg), and acesulfame potassium (20 mg) were then dissolved into the HPMC solution. The cooled solution was then sonicated for 2 minutes and placed in a vacuum for 5 minutes to remove trapped air, before casting onto a 60 $cm^2$ aluminium plate using a syringe. The plate was placed into an oven at 80° C. above the TGel, and allowed to dry overnight.

Eight 2×2 cm films from the same batch were tested for average drug content and weight. The results are shown in Table 6.

For comparison, the surface of blank films were sprayed with Naloxone. After casting, the blank films were loaded with Naloxone by a method of spraying. An airbrush was used to disperse a fine layer of 25 mg/mL naloxone HCL solution onto the surface of the films. Each side was sprayed for approximately 2 seconds. They were then placed into an oven at 60° C. for 10 minutes, to dryness.

TABLE 6

Drug content and weight of 2 × 2 cm Naloxone film

| Average Film Weight (mg) | Average Naloxone Concentration (µg/ml) | Average Amount of Naloxone (µg) in 1 mg of film |
|---|---|---|
| 8.4 | 22.07 | 26.27 |
| 11.8 | 30.00 | 25.40 |
| 14.4 | 37.72 | 26.19 |
| 8.9 | 23.72 | 26.65 |
| 8.2 | 21.65 | 26.40 |
| 13.1 | 31.24 | 23.85 |
| 11.8 | 35.27 | 29.89 |
| 8.6 | 22.55 | 26.22 |

Examples 17-22

Films are prepared as in Example 16. But the amounts of citric acid (cit) and acesulfame K (ace) are varied and the effects on on the physical properties of film are shown in Table 7.

TABLE 7

Effects of citric acid and acesulfame K

| Film | Average Thickness | Tensile strength | % Elongation | Folding Endurance Average | Film pH |
|---|---|---|---|---|---|
| 0.1 Cit. | 0.046 | 25.14 | 6.86 | 100+ | 6.2 |
| 0.25 Cit. | 0.047 | 28.27 | 12.37 | 50 | 5.9 |
| 0.5 Cit. | 0.051 | 17.9 | 5.94 | 38 | 4.5 |
| Cit. 0.5% Ace. 0.5% | 0.086 | 2.61 | 12.86 | 32 | 4.6 |
| 0.75% Cit. | 0.064 | 12.59 | 5.31 | 9.7 | 3.9 |
| 1% Cit. | 0.059 | 11.46 | 4.74 | 6 | 3.1 |

Figure 13:
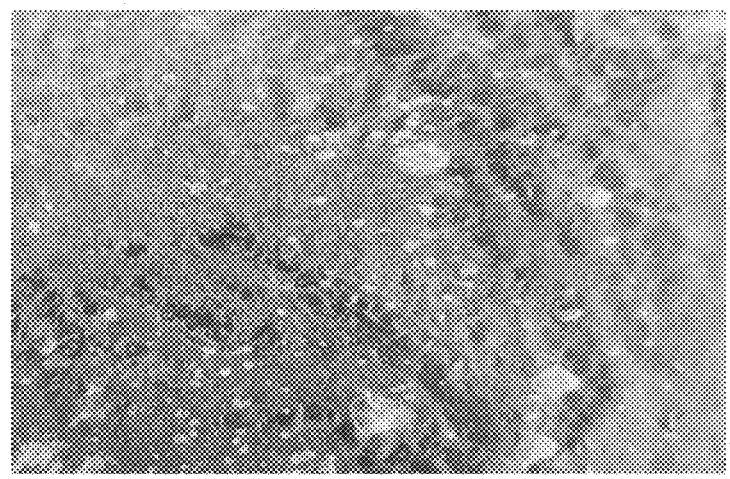
FIG. 13 is an unmagnified image of an ODF according to the present disclosure containing 0.5% acesuflame K, 0.5% citric acid and 20% PEO.
Figure 14:
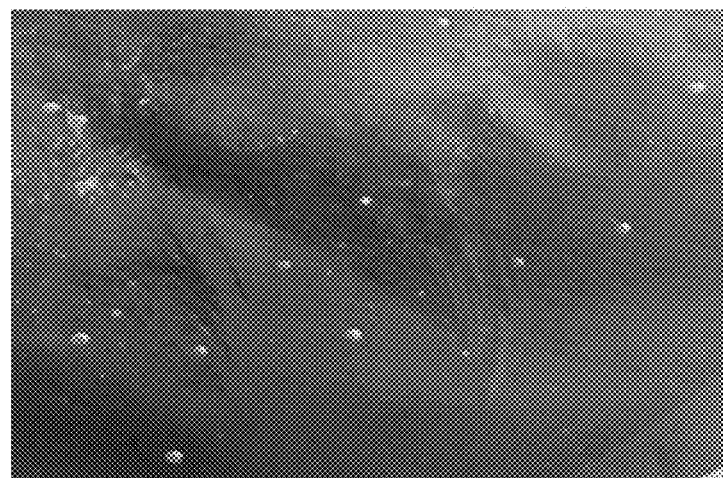
FIG. 14 is an unmagnified image of an ODF according to the present disclosure containing 0.5% citric acid and 20% PEO.

FIGS. 13 and 14 are unmagnified images of HPMC films containing 0.5% acesuflame K, 0.5% citric acid and 20% PEO (FIG. 13) and 0.5% citric acid and 20% PEO (FIG. 14). A comparison of these images shows the comparative effects citric acid and acesulfame K have on the physical appearance of the films. Most notably, higher concentration of citric acid correlated with generally lower tensile strength and % elongation. This is further supported by the data collected on folding endurance which shows a relationship between the amount of citric acid in the film and brittleness.

Film thickness and its correlation with distingration time is shown in Table 8. In general, thicker films had a slower disintgration time and tended to be more brittle (as measured by folding endurance.)

TABLE 8

Relationship between film thickness and other film physical properties

| Volume of HPMC (mL) | Film thickness (µm) | Mass of film (mg) | Disintegration time (s) | Folding endurance (No. of folds) |
|---|---|---|---|---|
| 15 | 70 +/− 15 | 350 | 243 | 71 |
| 12 | 45 +/− 10 | 305 | 44 | 93 |
| 8 | 40 +/− 5 | 207 | 25 | 100+ |
| 5 | 35 | 161 | 20 | 100+ |

Figure 15:
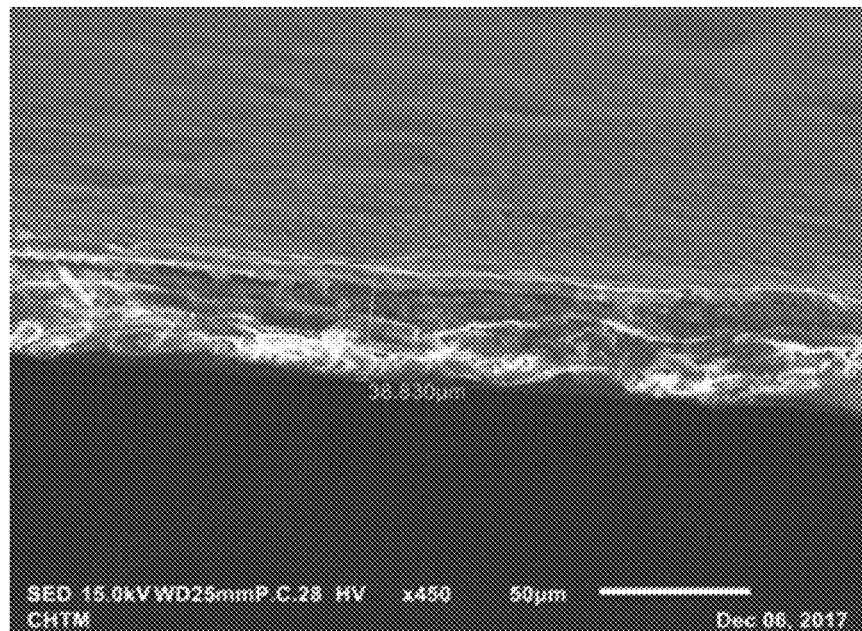
FIG. 15 is an SEM image of the side profile of a naloxone containing film having a thickness of 38.8 µm.

FIG. 15 is an SEM image of the side profile of a naloxone containing film having a thickness of 38.8 µm.

Figure 16:
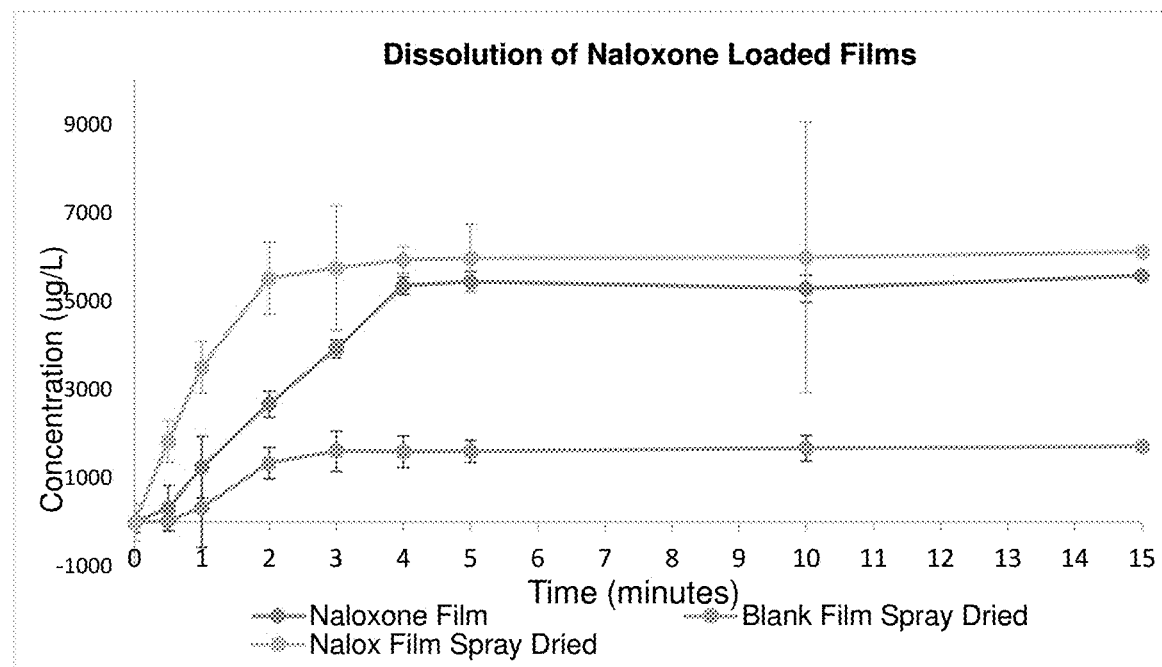
FIG. 16 is a graph comparing the dissolution of naloxone containing ODFs according to the present disclosure (NCF), NCF+naloxone sprayed (NS) on surface, and NS+blank films.

A more rapid and biphasic drug release occurs when naloxone is coated onto the surface of films that additionally contain naloxone. FIG. 16 compares the dissolution of naloxone containing films (NCF), NCF+naloxone sprayed (NS) on surface, and NS+blank films. The sprayed naloxone containing films, showed more rapid initial release. The fastest release occurs within the first 2 minutes. This is followed by a slower release of naloxone from 2-4 minutes. In all films tested, complete dissolution took place within 4 minutes.

Figure 17:
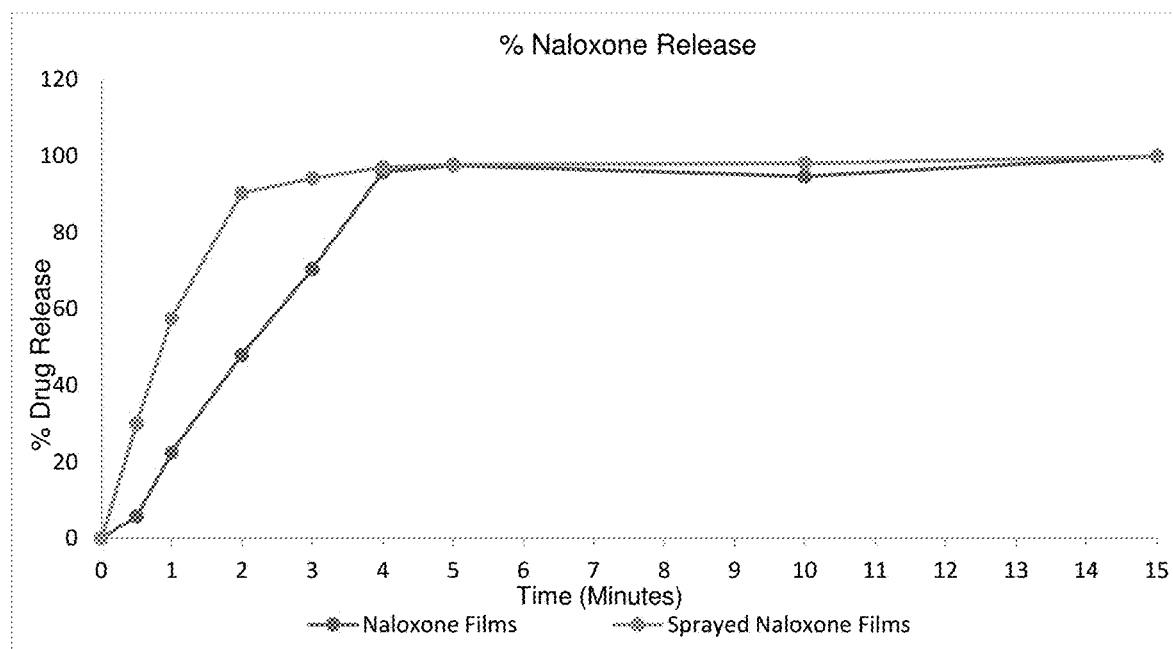
FIG. 17 is a graph showing the effect spraying as a method of drug loading has on the % drug release.

FIG. 17 shows the effect spraying as a method of drug loading has on the % drug release. Naloxone films which had not been sprayed show a generally linear drug release. In contrast, sprayed Naloxone films show a rapid initial release followed by a drastic slowdown from 2-4 minutes representing the last 10% of the dose. After 1 minute, approximately 3 times more of the total dose is released from the sprayed naloxone containing film compared with the non-sprayed naloxone containing films.

Examples 23-30 IV— Ibuprofen Containing ODFs

HPMC-based ODFs were formed as follows: 6 g of HPMC was weighed into weighing boat on a balance (TA Instruments waters LLC, Delaware, USA). Water was boiled and approximately 50 mL of just boiled water was added to a 100 ml glass beaker. 6 g of HPMC was dispersed into the hot water and temperature was maintained at approximately 85° C. HPMC was added slowly to ensure dispersion. The solution was then cooled by adding the remaining weight of ice slowly under stirring (to make 100 g of water solution in total) and allowed to cool, allowing the HPMC to dissolve at <30° C. to form a clear viscous solution.

Ibuprofen-containing ODFs were formed following the above methodology except after the solution of 6% HPMC in water was made, 1 g of ibuprofen was weighed and added while mixing. The solution was left overnight while stirring.

Films were cast as follows: an aluminum plate was attached onto the K control coater device (R K Printcoat Instruments Ltd, Herts, United Kingdom). Appropriate coating bar was selected and put into the latch mechanism. The speed of the K control coater device was set to 2. Cast solutions were left overnight to ensure complete drying, and film formation.

The following films were made:
PRT—6% HPMC solution cast at RT for 30 mins.
IBURT—6% HPMC, 1% Ibuprofen solution cast at RT for 30 mins.
P70—6% HPMC solution cast at 70° C. for 30 mins
IBU70—6% HPMC, 1% Ibuprofen solution cast at 70° C. for 30 mins
FILMB—6% HPMC solution cast at 40° C., then placed in the oven at 60° C.

FILMBSIL—6% HPMC solution cast at 40° C. for 10 minutes, then placed in oven at 60° C. for 24 hours. Silicone sprayed on surface of aluminum plate before casting.

FILMF 6%—HPMC solution cast at 70° C. for 10 minutes, then placed in oven at 60° C. for 24 hours.

FILMFSIL—6% HPMC solution cast at 70° C. for 10 minutes, then placed in oven at 60° C. for 24 hours. Silicone sprayed on surface of aluminium plate before casting.

Examples 31-37 Addition of Ethyl Cellulose to HPMC Films

Methocel E50 (6% w/w) solution were prepared as in Example 9 but with the initial water temperature at 70° C. before the addition of ice. Ethyl cellulose (EC) was added at 1% w/w during the dispersion mixing phase (Formulation EC1).

Using the method above, the concentration of ethyl cellulose was then reduced to 0.25% w/v, and the casting temperature raised to 80° C., to cast at a temperature well above the thermal gelation temperature (Formulation EC2). Additionally, an 8% w/v E50 solutions containing 0.25% EC was prepared (Formulation EC3).

A further three solutions were prepared as above, but by using 50 mL, 10 mL, or 5 mL pure ethanol (added as a cosolvent) to the prepared 8% w/v E50 HPMC solution and then adding 0.25% w/v EC dispersion phase (Formulations EC4-EC6 respectively).

Dispersions were cast at 70° C. and left to set for approximately 30 minutes.

8% w/v Methocel E50 was prepared in the same way as above, but 0.25% EC w/w was added to the solution as corresponding volumes of Aquacoat or Surelease. These were also added during the HPMC dispersion phase (Formulations EC7-EC8 respectively).

The ethylcellulose could not be uniformly distributed in EC1-EC6 and showed high particles counts under images analysis indicative of EC clumping. EC7 and EC8 demonstrated low particle counts demontrating a uniform distribution of EC and no clumping (Table #).

TABLE 9

Average particle count for films.

| Sample | Average Particle Count |
|---|---|
| EC1 | 1724 |
| EC2 | 488 |
| EC3 | 279 |
| EC7 | <5 |
| EC8 | <5 |

Figure 18:
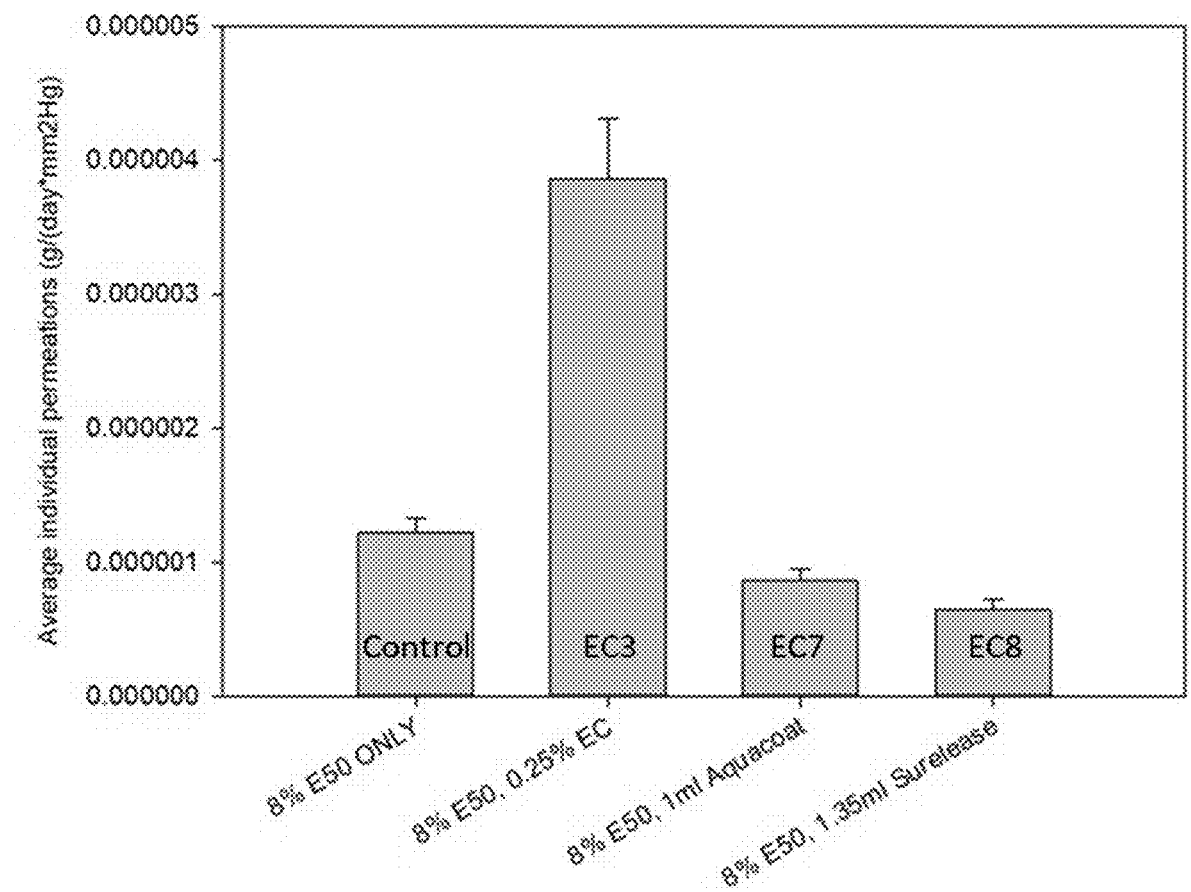
FIG. 18 is a graph of vapor permeation data for ethyl cellulose containing ODFs according to the present disclosure.

Vapor permeation data indicated that the EC7 and EC8 films allowed less water to permeate through films then other films using a standardized test (FIG. 18), demonstrating their increased hydrophobicity. Surprizingly the incorporation of EC as a powder demonstrated increased permeability of vapor (indicating that it did not improve hydrophobicity of the film when added this way).

What is claimed is:

1. An orodispersible film (ODF) formed by a method comprising:
    forming a mixture of a thermally gelling polymer, a solvent, and one or more ingredients including at least one active pharmaceutical ingredient (API), wherein the mixture has a thermal gelling point;
    forming a stable solidified gel with a uniform distribution of the at least one API by casting the mixture onto a heated substrate wherein the temperature of the substrate is at or above the thermal gelling point for the mixture; and
    dehydrating the stable solidified gel, thereby forming a film wherein the API is uniformly distributed throughout the film.

2. The ODF of claim 1 wherein the method further comprises adding one or more gelling aid to the mixture so as to reduce the thermal gelling point of the mixture.

3. The ODF of claim 2 wherein the gelling aid reduces the thermal gelation point of the mixture to a suitable temperature for processing of the one or more ingredients.

4. The ODF of claim 1 wherein the thermally gelling polymer is hydroxypropyl methylcellulose (HPMC).

5. The ODF of claim 1 wherein the one or more ingredients include a hydrophobic ingredient.

6. The ODF of claim 1 wherein the API is hydrophobic.

7. The ODF of claim 1 wherein the API is Itraconazole.

8. The ODF of claim 1 wherein the API is Naloxone.

9. The ODF of claim 1 wherein the API is Ibuprofen.

10. The ODF of claim 1 wherein the one or more ingredients include an excipient.

11. The ODF of claim 10 wherein the excipient is hydrophobic.

12. The ODF of claim 11 wherein the hydrophobic excipient is ethyl cellulose.

13. The ODF of claim 1 further comprising an ingredient that has been applied to the surface of the film after it is formed.

14. The ODF of claim 13 wherein the ingredient applied to the surface is an API.

15. The ODF of claim 1 wherein the API is uniformly distributed in such a way that there is no visible clumping of the API.

16. An orodispersible film (ODF) wherein an active pharmaceutical ingredient (API) is uniformly distributed through the film in such a way that there is no visible clumping of the API.

17. The ODF of claim 16 wherein the API is hydrophobic.

18. The ODF of claim 16 wherein the API is Itraconazole.

19. The ODF of claim 16 wherein the API is Naloxone.

20. The ODF of claim 16 wherein the API is Ibuprofen.

* * * * *